(12) United States Patent  (10) Patent No.: US 7,742,071 B2
Kennedy et al.  (45) Date of Patent: Jun. 22, 2010

(54) METHODS AND APPARATUS FOR INSPECTING CENTERPLANE CONNECTORS

(75) Inventors: John F. Kennedy, Oakley, CA (US); Chuck V. Ho, San Jose, CA (US); John S. Mew, Ceres, CA (US); Ricky A. Smith, Fremont, CA (US); Thomas E. Roach, Oakley, CA (US); Brian T. Evans, Mountainview, CA (US); Greg I. Henry, San Jose, CA (US)

(73) Assignee: Oracle America, Inc., Santa Clara, CA (US)

( * ) Notice: Subject to any disclaimer, the term of this patent is extended or adjusted under 35 U.S.C. 154(b) by 2186 days.

(21) Appl. No.: 10/351,618

(22) Filed: Jan. 23, 2003

(65) Prior Publication Data

US 2004/0148128 A1 Jul. 29, 2004

(51) Int. Cl.
*H04N 9/47* (2006.01)
*G06K 9/00* (2006.01)

(52) U.S. Cl. .......................................... 348/87; 382/147
(58) Field of Classification Search ................... 348/87, 348/92, 94, 95; 382/145, 147; 250/358.1; 356/239.5; 361/818
See application file for complete search history.

(56) References Cited

U.S. PATENT DOCUMENTS

| | | | |
|---|---|---|---|
| 5,455,870 A | 10/1995 | Sepai | |
| 5,574,801 A | 11/1996 | Collet-Beillon | |
| 5,583,948 A | 12/1996 | Shibayama | |
| 5,686,994 A | 11/1997 | Tokura | |
| 5,739,846 A | 4/1998 | Gieskes | |
| 6,141,040 A | 10/2000 | Toh | |
| 6,151,063 A * | 11/2000 | Nishikawa | 348/92 |
| 6,681,038 B2 | 1/2004 | Vilella | |
| 6,914,672 B2 * | 7/2005 | Yagita | 356/239.5 |
| 2001/0040217 A1 * | 11/2001 | Mizuoka et al. | 250/358.1 |
| 2003/0048625 A1 * | 3/2003 | Ishii et al. | 361/818 |

OTHER PUBLICATIONS

TSR Series II Single-Port Dual Slot OC-192c / STM 64c Install pp. 12 22; http://www.avici.com/documentation/htmlDocs/03481-01-revBA/03...806/20/2002.

* cited by examiner

*Primary Examiner*—Gims S Philippe
(74) *Attorney, Agent, or Firm*—Meyertons, Hood, Kivlin, Kowert & Goetzel, P.C.

(57) ABSTRACT

The present invention relates to apparatus and methods that reliably detect defects on centerplane connectors. The apparatus and methods include a visual inspection system. The visual inspection system includes a control box, an inspection cart, a camera jig, and a vision system. The vision system has a light emitting diode (LED) lighting system that provides the necessary lighting for the camera on the vision system. The vision system is mounted to the camera jig via a spring-loaded mechanism. The camera jig has dimensions similar to a daughter card that is used with the centerplane connectors. The camera jig also includes a motor and worm gear assembly that raise and/or lower the camera's view of the centerplane connectors. The control box is mounted to the inspection cart so that an operator can use it to control the up/down movements of the vision system. A timer/relay may be build into the control box to allow controlled/fixed movements of the vision system. The camera is connected to a high resolution color monitor and/or an optional flat screen color monitor. A computer workstation can be used to video capture the camera's image and can be used to send this image to an e-mail alias/webpage or print out a hard copy.

20 Claims, 6 Drawing Sheets

METHODS AND APPARATUS FOR INSPECTING CENTERPLANE CONNECTORS

BACKGROUND OF THE INVENTION

1. Field of the Invention

The present invention relates to connectors for connecting circuit boards. More particularly, the present invention relates to apparatus and methods for detecting defects of connectors on circuit boards.

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

Sun, Sun Microsystems, the Sun logo, Sun Fire, 3800-6800 Midframe, Ultra, Solaris, and all Java-based trademarks and logos are trademarks or registered trademarks of Sun Microsystems, Inc. in the United States and other countries. The VHDM trademark is used under license and is a trademark of Teradyne, Inc. in the United States and other countries. All SPARC trademarks are used under license and are trademarks of SPARC International, Inc. in the United States and other countries. Products bearing SPARC trademarks are based upon an architecture developed by Sun Microsystems, Inc.

2. Description of Related Art

Most computer systems include a connection structure for connecting printed circuit boards of the computer system together (e.g., central process unit boards, memory boards, etc.). One such connection structure includes a circuit board that serves as a centerplane. The centerplane (or backplane) has a set of centerplane connectors mounted to the centerplane. For such structure, the computer system also includes another circuit board called a daughter card that has card connectors that mate with the centerplane connectors. That is, the centerplane connectors and the card connectors typically include corresponding sets of contacts, respectively. For example, pins and pin-receiving sockets, which are configured to make electrical contact with each other when the centerplane connectors and the card connectors mate.

Installation of a daughter card into a computer system typically involves a user sliding the daughter card into an opening of a card cage of the connection structure. The centerplane typically resides the rear end of the card cage, or in the middle of the card cage if the card cage is configured to receive daughter cards through both ends. As the daughter card slides within the card cage, card connectors along the edge of the daughter card eventually engage centerplane connectors mounted to the centerplane at the rear or in the middle of the card cage. After the card connectors make electrical contact with the centerplane connectors, the user continues to slide the daughter card further into the card cage until the daughter card moves into a fully-seated position within the card cage. The user can repeat this installation process for other daughter cards as well.

To avoid damage to the daughter card and/or the centerplane, a detailed inspection of the centerplane connectors is required before inserting the card connectors into the centerplane connectors. The centerplane connectors should be inspected for mechanical defects such as bent and/or damaged pins on the centerplane connectors. The detected defects need to be remedied prior to insertion of the daughter card or the defects may spread into other connectors and on to the daughter card. However, because of the larger number of relatively small contacts on each of the centerplane connectors (e.g., a central processing unit (CPU) connector may have 840 pins, a repeater board (RP) may have 1400 pins, an input/output (I/O) may have 560 pins), the prior arts were unable to reliably spot damages on the centerplane connectors.

Accordingly, there is a need to provide apparatus and methods that reliably detect defects on the centerplane connectors. That is, it would be desirable to provide an inspection system that can reliably spot damages on centerplane connectors having a larger number of relatively small contacts.

SUMMARY OF THE INVENTION

The present invention relates to methods and apparatus that reliably detect defects on centerplane connectors. In one embodiment of the present invention, a visual inspection system is designed to reliably spot damages on centerplane connectors having a larger number of relatively small contacts (e.g., pins). For example, a central processing unit (CPU) connector on a centerplane may have 840 pins and the centerplane may have 6 CPU connectors, which would raise the total pin count for inspection to 5040 pins.

The invention is directed to an inspection system for detecting defects on connectors of a centerplane. In an embodiment of the invention, the inspection system includes a video monitor, a camera jig, a jig cradle having a jig holder for holding the camera jig, a vision system connected with the video monitor and the camera jig, and a control box connected with the vision system and the camera jig. The camera jig may include a spring for connecting the vision system with the camera jig. The spring provides the vision system with an amount of perpendicular movement with respect to the centerplane connectors being inspected. In one embodiment, the camera jig simulates a daughter card that is to be used with the centerplane.

In another embodiment of the invention, a camera jig that simulates a daughter card is provided. The camera jig is installed on to an inspection system. A vision system on the camera jig is activated. A button to inspect a first sequence of contacts on a connector of the centerplane is pushed. The first sequence of contacts is inspected for defects. Any inspected defects and their specific location are recorded. The button is again pressed to inspect a second sequence of contacts on the connector. The first sequence of contacts does not overlap with the second sequence of contacts.

A more complete understanding of the present invention will be afforded to those skilled in the art, as well as a realization of additional advantages and objects thereof, by a consideration of the following detailed description of the embodiment. Reference will be made to the appended sheets of drawings, which will first be described briefly.

BRIEF DESCRIPTION OF THE DRAWINGS

The drawings illustrate the design and utility of preferred embodiments of the invention. The components in the drawings are not necessarily to scale, emphasis instead being placed upon illustrating the principles underlying the embodiment. Moreover, in the drawings, like reference numerals designate corresponding parts throughout the different views.

DETAILED DESCRIPTION

The present invention is directed to methods and apparatus that reliably detect defects on centerplane connectors. In one embodiment of the present invention, a visual inspection system is designed to reliably spot damages on centerplane connectors that have a large number of relatively small contacts (e.g., pins). For example, a central processing unit (CPU) connector on a centerplane may have 840 pins, and the centerplane may have 6 CPU connectors, which would raise the total pin count for inspection to 5040 pins.

FIGS. 1-7 illustrate a visual inspection system 100 for inspecting connector defects on a centerplane 1001 in an embodiment of the present invention. The visual inspection system 100 includes a vision system 110, a video monitor 28, a control box 57, a camera jig 120, a jig cradle 38, an inspection cart 27, and a centerplane chassis 1009. The centerplane chassis 1009 is designed to hold the centerplane 1001 that has the centerplane connectors 1003 being inspected by the inspection system 100. In one embodiment, the centerplane 1001 has centerplane connectors 1003 for six central processing unit (CPU) daughter cards, one repeater board (RP) daughter card, four input/output (I/O) daughter cards, and/or two separate system controller (SC) daughter cards. In another embodiment of the present invention, the centerplane connectors 1003 to be inspected are in a modular electrical connector system. The modular electrical connector system may be a high speed and high density electrical connector system, such as a connector system having the trade name: VHDM®, manufactured by Teradyne Incorporated.

In FIGS. 1, 3-5, and 7, the jig cradle 38 may be attached to the inspection cart 27 by at least one connector 70 on the jig cradle 38. The jig cradle 38 may also contain at least one jig holder 72 for holding the camera jig 120 in a predetermined position (i.e., to act as a housing for the camera jig 120). Alternatively, the jig cradle 38 may be attached to the centerplane chassis that is holding the centerplane.

In FIGS. 1-2 and 4-6, the vision system 110 of the inspection system 100 has a lighting system 37, such as a light emitting diode (LED) lighting system, connected to a camera cover 60. The lighting system 37 provides the necessary lighting for a inspection camera 39, such as a small video camera having a short focal point or a video camera dimensioned similar to the size of a typical lipstick holder. The camera 39, the lighting system 37, and their associated subassemblies, such as camera cover 60, are mounted to the camera jig 120 via a camera mount 36.

In an embodiment of the present invention, the camera jig 120 simulates a daughter card that is to be used with the centerplane. In another embodiment, the camera jig 120 provides the vision system 110 with a view point similar to the daughter card connectors that are to be inserted with the centerplane connectors. The camera jig 120 may be designed and/or dimensioned to be the same size as a daughter card that is to be used with the centerplane. Thus, if the CPU connectors on the centerplane are to be inspected by the inspection system 100, the camera jig 120 is designed and/or dimensioned to be the same size as a CPU daughter card (i.e., a circuit board containing at least one CPU). Alternatively, if the inspection system 100 is inspecting system controller (SC) centerplane connectors, I/O centerplane connectors, and/or RP centerplane connectors, the camera jig 120 should be designed and/or dimensioned to be the same size(s) as the daughter card(s) containing the SC, I/O, and/or RP device(s). In one embodiment, the jig 120 is and/or are dimensioned to be the same as Sun Fire™ midframe daughter cards used in Sun Microsystems's 3800, 4800, 4810, & 6800 Midframe™ servers.

Figure 2:
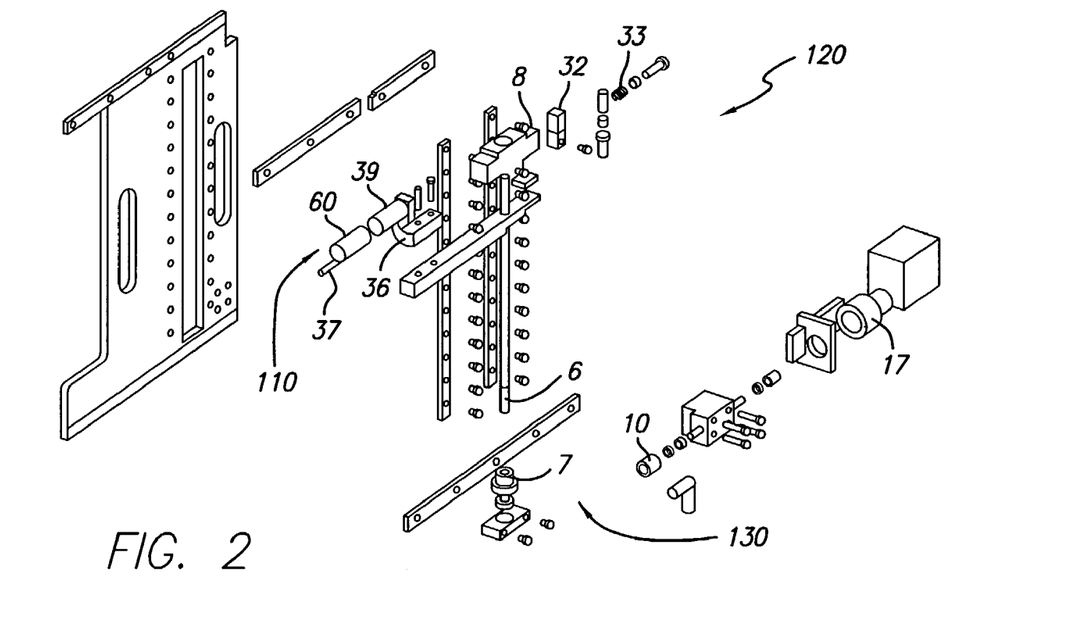
FIG. 2 is an exploded perspective view of a camera jig, a vision system, and a worm gear assembly of FIG. 1.
Figure 3:
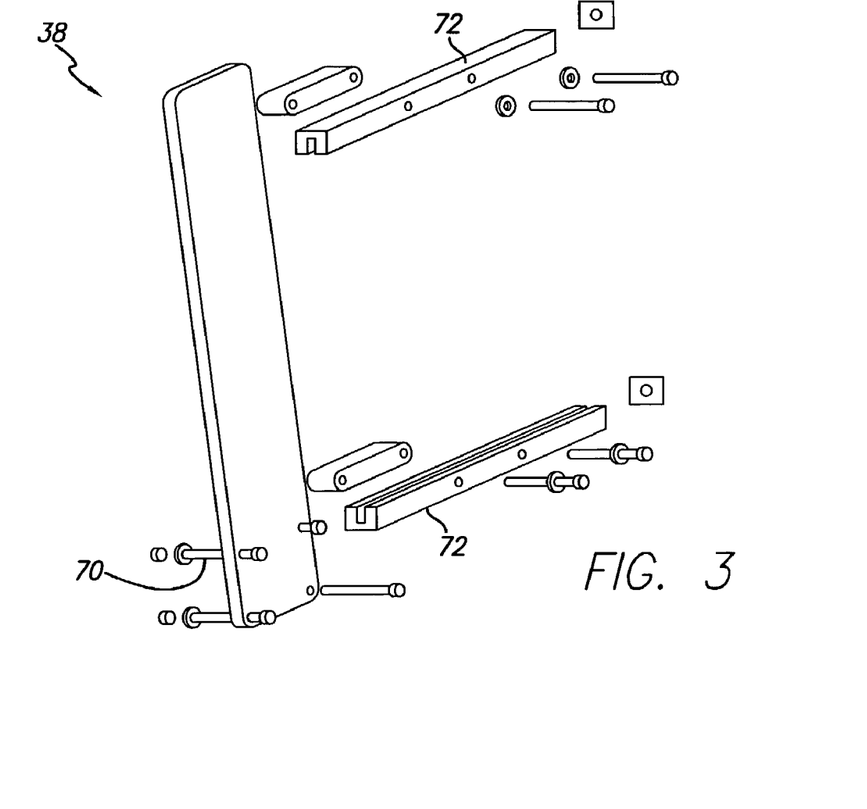
FIG. 3 is an exploded perspective view of a jig cradle of FIG. 1.
Figure 6:
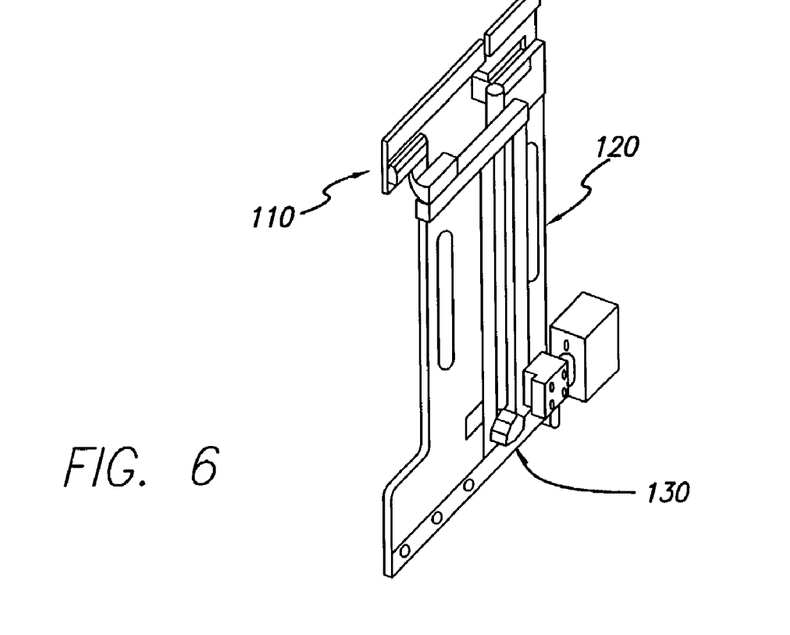
FIG. 6 is a perspective view of the camera jig, the vision system, and the work gear assembly of FIG. 2.
Figure 7:
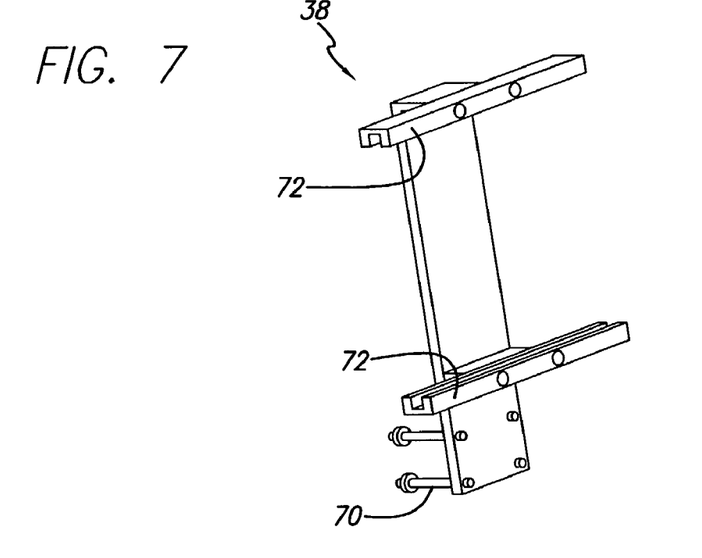
FIG. 7 is a perspective view of the jig cradle of FIG. 3.

In FIGS. 2 and 6, the camera jig 120 may comprise a motor 17, such as a 12 Vdc (a 12 volts and direct current) motor, and a gear assembly 130, such as a worm gear assembly. The worm gear assembly 130 is comprised of a worm gear 7, a worm 10 (e.g., a precision worm), and a worm gear rod 6 (e.g., a long rod having a lead screw). The motor 17 and the gear assembly 130 raise and/or lower the vision system 110 (i.e., the camera's view of the centerplane connectors).

In FIG. 2, the camera jig 120 may also be a spring-loaded camera jig. The spring-loaded camera jig is comprised of a spring 33 connected with a spring block 32. The spring block 32 is connected with a carriage mount 8. The carriage mount 8 is connected with the camera mount 36 and the worm gear rod 6. The spring 33 may be used to adjust a horizontal position (e.g., a x-axis position) of the vision system 110 on the camera jig 120 and/or to function as part of a protecting bumper for the vision system 110 (if, e.g., the vision system 110 is placed too close to a centerplane connector).

In FIGS. 1-2 and 4-6, the control box 57 may be mounted to a vision cart 27. The control box 57 allows an operator of the inspection system 100 to control the up/down movements of the vision system 110. The control box 57 is connected to a cameral control unit 29, such as a single push button control switch. Alternatively, the camera control unit 29 may comprise a up-down switch and a start button. A timer/relay may also be built into the control box 57 to allow controlled fixed movements of the vision system 110 for ease of inspection. In one embodiment, the control box 57 allows for connector inspections that do not overlap.

Figure 8:
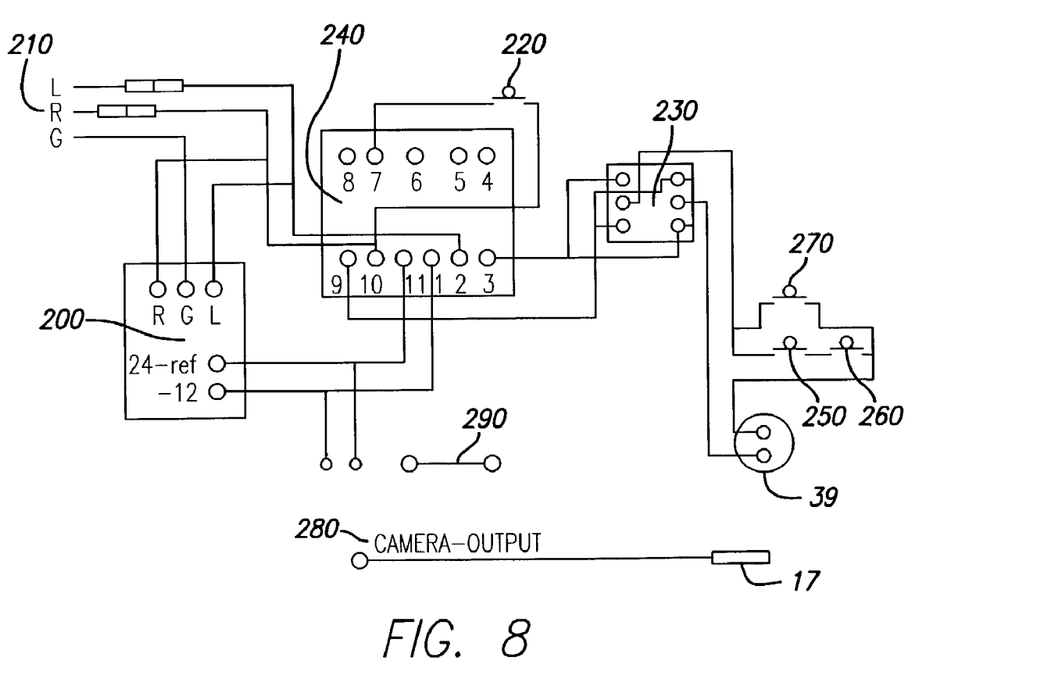
FIG. 8 shows an interconnection of a control box according to an embodiment of the invention.

FIG. 8 shows an exemplary interconnection of the control box 57 in an embodiment of the present invention. In FIG. 8, the control box 57 comprises a power supply 200, a camera control unit 280, and a video connector 290 for connecting the control box 57 with the video monitor 28. The camera control unit 280 is connected with motor 17. The power supply 200 receives its electrical power from a power entry 210 and is connected with a start button (or switch) 220 and an up-down switch 230 via a connection pole 240. The up-down switch 230 is connected with the inspection camera 39. The up-down switch 230 is also connected with a top-stop switch 250 and a bottom-stop switch 260. The top-stop switch 250 and the bottom-stop switch 260 respectively may be used to stop the movements of the inspection camera 39 when it has reached the top and bottom ends of a rod (e.g., the worm gear rod 6 in FIG. 2). The up-down switch 230 may also be connected with an autowrite switch 270. The autowrite switch 270 may be used to stop the movements of the inspection camera 39 after it has moved a predetermined amount of distance on a rod (e.g., the worm gear rod 6 in FIG. 2).

Figure 1:
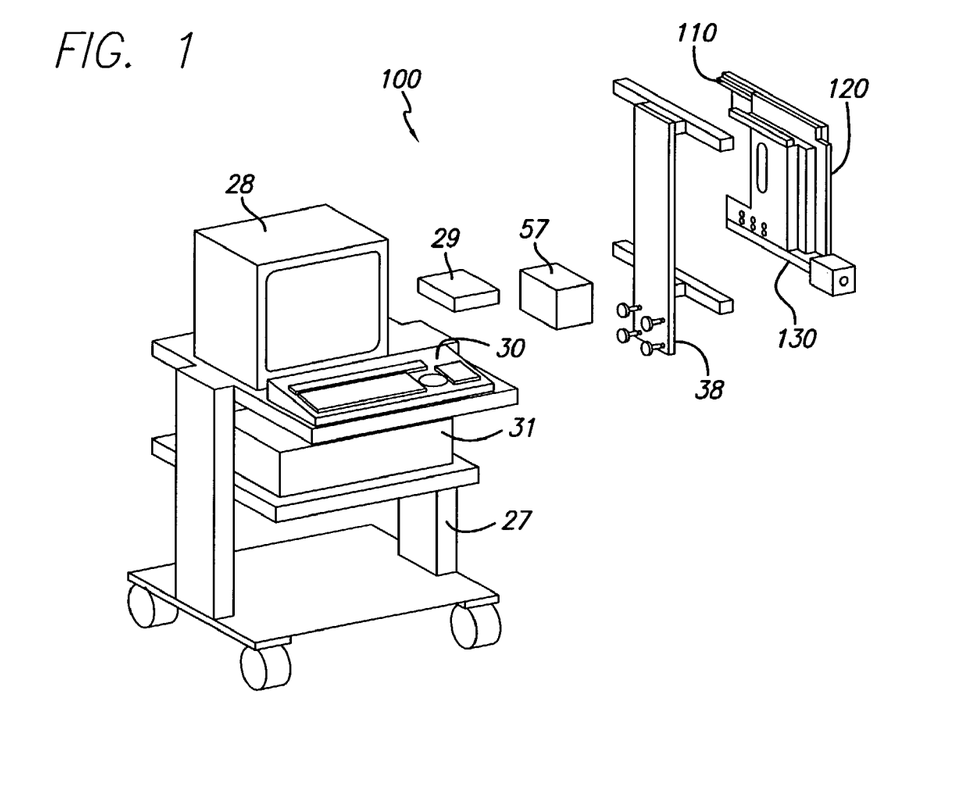
FIG. 1 is an exploded perspective view of an inspection system according to an embodiment of the invention.
Figure 4:
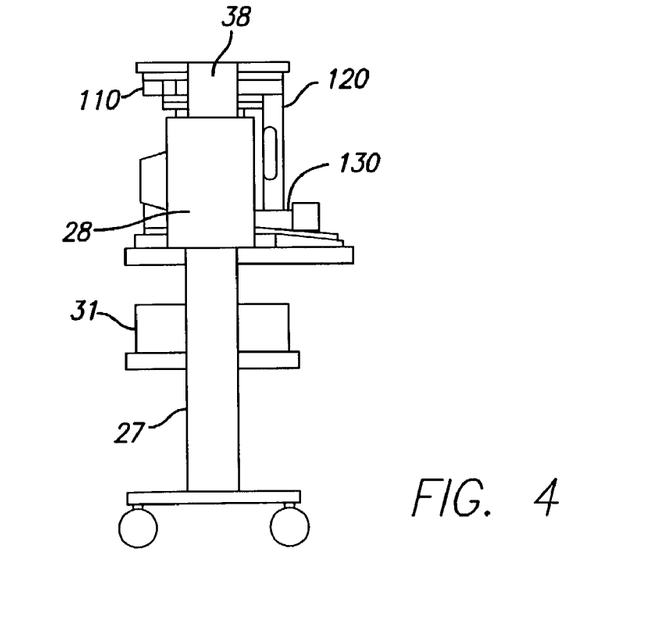
FIG. 4 is a side view of the inspection system of FIG. 1.
Figure 5:
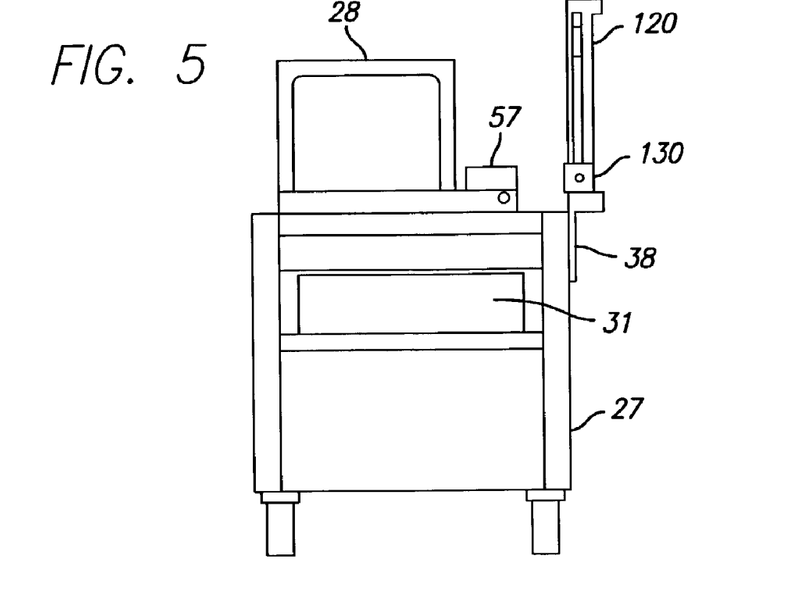
FIG. 5 is a front face view of the inspection system of FIG. 1.

In FIGS. 1 and 4-5, the inspection camera 39 may be connected with the video monitor 28, such as a high-resolution color monitor and/or a flat screen color monitor. The video monitor 28 is connected with a computer 31, such as a Sun Microsystems's Ultra-2™ workstation. The computer 31 may be used to video capture the camera's image. The computer 31 may also be used to send the captured image to an e-mail alias/webpage or print out a hard copy.

In one embodiment of the present invention, the visual inspection system 100 may also include a keyboard 30 connected to the computer 31. The keyboard may be used to enter camera calibration and/or other information into the inspection system 100. A second color monitor (not shown) may also be connected to the computer. The second monitor may be used in assisting the entry of the camera calibration and/or other information into the inspection system 100.

In general according to the foregoing, an operator of the inspection system 100 only needs to control three things on the inspection system 100. The three things are: (1) a start button (e.g., 220 in FIG. 8) for powering on the vision system 110; (2) an up/down switch (e.g., 230 in FIG. 8) for moving the camera 39 up/down; and (3) a horizontal adjustment gear (not shown) for adjusting the horizontal position of the vision system 110. The horizontal adjustment may comprise a rotating finger nut to allow the inspector to manually adjust the vision system's horizontal position by rotating the finger nut. The start button may also be used as a reset switch when the operator changes the direction of the camera inspection motions. In addition, the start button may be used by the operator to inspect a plurality of inspection sequences (e.g., by pressing the start button to automatically inspect a first sequence or series of contacts and pressing the same button again to automatically inspect a second series of contacts).

Figure 9:
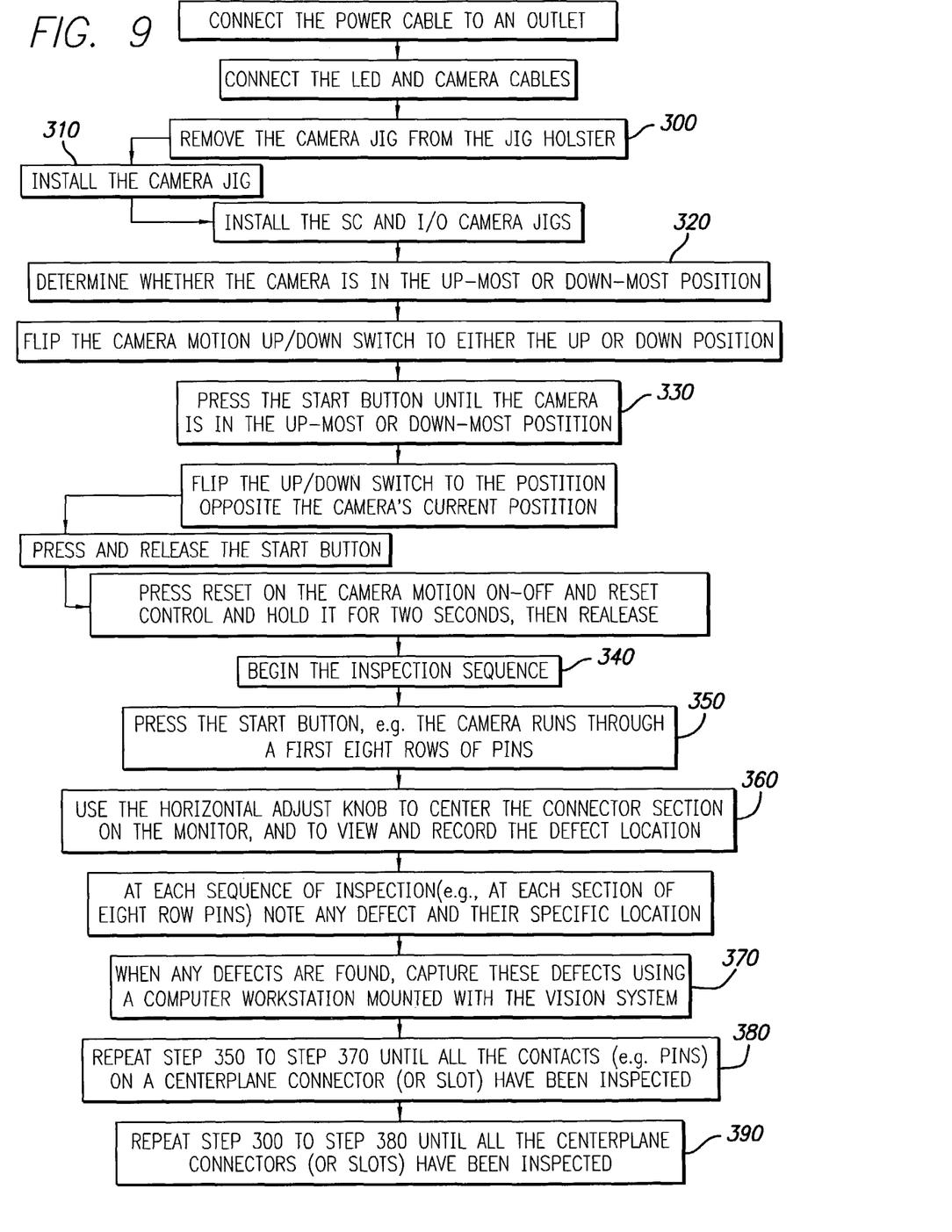
FIG. 9 is a flow diagram showing exemplary steps of a method according to the invention.
Figure 10:
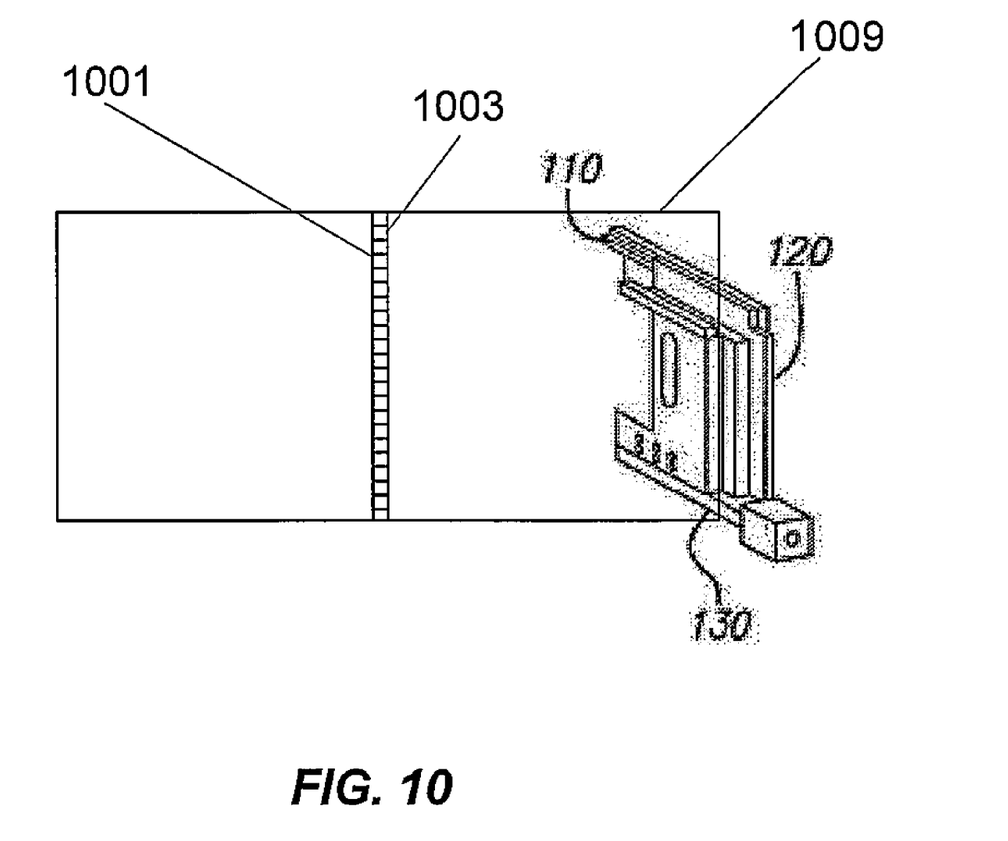
FIG. 10 illustrates a general depiction of a camera jig in a centerplane chassis with a centerplane, according to an embodiment.

In operation, the present invention provides a method for inspecting damages on centerplane connectors 1003 having a large number of relatively small contacts, as diagrammed in FIG. 9. At step 300 of FIG. 9, the camera jig (e.g., 120) is removed from a protective storage holster (not shown). The jig (e.g., 120) simulates a daughter card that is to be used with and/or inserted into the centerplane that is to be inspected. At step 310, the camera jig (e.g., 120) is installed onto the inspection system (e.g., 100) and/or the centerplane chassis 1009 (e.g., as generally depicted in FIG. 10) that is designed to hold the centerplane 1001 that is to be inspected. An operator and/or the inspection system (e.g., 100) then determines whether the inspection camera (e.g., 39) is located in an up-most or down-most inspection position at step 320. If the camera is not located in either the up-most or down-most position, the operator may flip the up-down switch (e.g., 230) to either the up or down position and then press a start button (e.g., 220) after the camera (e.g., 39) is in the up-most and/or down-most position at step 330. The operator may also flip the up-down switch (e.g., 230) to the position opposite the camera's current position and press and release the start button (e.g., 220). The operator may then press a separate reset control button or the same start button (e.g., 220) and begin the inspection sequence at step 340. The operator then presses the start button to inspect a first sequence of contacts on the centerplane connectors 1003, for example, the camera (e.g., 39) inspects a first eight-rows of pins in the first inspection sequence at step 350. The operator may then use the horizontal adjust knob to center the connector section on the monitor (e.g., 28) and view and record the defected location on the centerplane connectors 1003 at step 360. Upon the detection of any defects, its specific location (e.g., a bent pin) is recorded and captured using a computer (e.g., 31) at step 370. The inspection method then repeats steps 350 to 370 until all the contacts on a centerplane connector 1003 have been inspected at step 380. The inspection method then repeats steps 300 to 380 until all the connectors on the centerplane 1001 have been inspected at step 390.

Embodiments of the invention can be implemented as a computer firmware and/or computer software in the form of computer-readable program code executed in a general purpose computing environment; in the form of bytecode class files executable within a Java™ run time environment running in such an environment; in the form of bytecodes running on a processor (or devices enabled to process bytecodes) existing in a distributed environment (e.g., one or more processors on a network); as microprogrammed bit-slice hardware; as digital signal processors; or as hard-wired control logic. In addition, the computer and circuit system described above are for purposes of example only. An embodiment of the invention may be implemented in any type of computer and circuit system or programming or processing environment.

Having thus described embodiments of the present invention, it should be apparent to those skilled in the art that certain advantages of the within inspection system have been achieved. It should also be appreciated that various modifications, adaptations, and alternative embodiments thereof may be made within the scope and spirit of the present invention. For example, a centerplane and a daughter card assembly has been illustrated, but it should be apparent that the inventive concepts described above would be equally applicable to other types of computer circuit board assembly. The invention is further defined by the appended claims.

What is claimed is:

1. A system, comprising:
    an electronic chassis;
    a camera;
    a camera jig coupled to the camera; and
    wherein the camera jig is operable to position the camera along a plurality of camera positions inside the electronics chassis.

2. The system of claim 1,
    wherein the electronics chassis is a centerplane chassis; and
    wherein the camera jig is operable to position the camera to view a centerplane mounted in the centerplane chassis.

3. The system of claim 2, wherein at least a subset of the plurality of camera positions form an array that is substantially parallel to an array of centerplane connectors on the centerplane.

4. The system of claim 1, wherein the camera jig is operable to move the camera in a vertical direction.

5. The system of claim 1, further comprising:
    a control box coupled to the camera jig; and
    wherein the control box controls movement of the camera jig.

6. The system of claim 5, wherein the control box comprises a single push button control for allowing a plurality of inspection sequences by only pressing the single push button.

7. The system of claim 1, further comprising a video monitor operable to display a camera view from the camera.

8. The system of claim 1, further comprising a computer coupled to the camera for capturing an image of a defect of a connector inside the electronics chassis.

9. The system of claim 8, wherein the computer sends the captured image of the defect to a remote device; and wherein the remote device includes at least one of an e-mail receiving device, a webpage receiving device, or a printer.

10. The system of claim 1,
    wherein the camera is a video camera; and
    wherein the system further comprises a light emitting diode coupled to the video camera to provide light for the video camera.

11. The system of claim 1, wherein the camera jig has dimensions that are substantially similar to dimensions of a daughtercard operable to be received in the electronics chassis such that the camera jig is operable to be inserted into the electronics chassis to position the camera along a plurality of camera positions that substantially correspond with connectors in the electronics chassis that are operable to receive the daughtercard.

12. The system of claim 11, wherein the plurality of camera positions form a substantially continuous linear array of camera positions.

13. The system of claim 1, wherein the camera jig comprises:
a gear assembly;
a motor connected with the gear assembly;
wherein the motor moves the camera longitudinally on the camera jig; and
wherein the gear assembly comprises a worm gear assembly.

14. The system of claim 1, wherein the camera jig is a spring-loaded camera jig.

15. An inspection method, comprising:
providing a camera jig, coupled to a camera, wherein the camera jig is operable to position the camera along a plurality of camera positions;
inserting the camera jig into an electronics chassis;
aligning the camera of the camera jig with at least one connector inside the electronics chassis; and
capturing an image of the at least one connector with the camera.

16. The inspection method of claim 15, further comprising:
moving the camera on the camera jig along the plurality of camera positions;
wherein at least a subset of the plurality of camera positions are substantially parallel to an array of connectors inside the chassis; and
wherein the array of connectors includes the at least one connector.

17. The inspection method of claim 16,
wherein the array of connectors is comprised in a first sequence of connectors;
wherein another array of connectors is comprised in a second sequence of connectors;
wherein the first sequence does not overlap with the second sequence;
wherein the inspection method further comprises:
capturing an image of at least two connectors in the first sequence of connectors;
receiving an input to capture an image of at least part of the second sequence of connectors; and
capturing an image of at least two connectors in the second sequence of connectors in response to receiving the input.

18. The inspection method of claim 15, further comprising:
recording a defect in the image of the connector and a specific location of the defect.

19. A system, comprising:
a centerplane chassis comprising a centerplane;
a video monitor;
a camera jig;
a vision system, which includes a camera, coupled to the video monitor and the camera jig, wherein the camera jig is operable to position the vision system to view at least a subset of connectors of the centerplane with the camera;
a control box coupled to the vision system and the camera jig; wherein the control box comprises a relay for providing controlled movements of the vision system on the camera jig; and
a computer coupled to the vision system, wherein the computer is operable to capture images, provided by the vision system, of defects on the at least a subset of the connectors of the centerplane.

20. The system of claim 19,
wherein the camera jig has dimensions that are substantially similar to dimensions of a daughtercard operable to be received in the centerplane chassis housing the centerplane; and
wherein the camera jig is operable to be inserted into the centerplane chassis to position the vision system to view the at least a subset of connectors on the centerplane.

* * * * *

UNITED STATES PATENT AND TRADEMARK OFFICE
CERTIFICATE OF CORRECTION

| | | |
|---|---|---|
| PATENT NO. | : 7,742,071 B2 | Page 1 of 1 |
| APPLICATION NO. | : 10/351618 | |
| DATED | : June 22, 2010 | |
| INVENTOR(S) | : John F. Kennedy et al. | |

It is certified that error appears in the above-identified patent and that said Letters Patent is hereby corrected as shown below:

In column 1, line 45, after "resides" insert -- at --.

In column 3, line 7, after "invention;" delete "and".

In column 3, line 9, delete "invention." and insert -- invention; and --, therefor.

In column 7, line 3, in claim 11, delete "daughtercard" and insert -- daughter card --, therefor.

In column 7, line 8, in claim 11, delete "daughtercard." and insert -- daughter card. --, therefor.

In column 8, line 35, in claim 20, delete "daughtercard" and insert -- daughter card --, therefor.

Signed and Sealed this
Twenty-sixth Day of July, 2011

David J. Kappos
*Director of the United States Patent and Trademark Office*